United States Patent [19]

Dorlars et al.

[11] 4,233,440
[45] Nov. 11, 1980

[54] TRIAZOLYL-STILBENES

[75] Inventors: Alfons Dorlars, Leverkusen; Otto Neuner, Bergisch-Gladbach, both of Fed. Rep. of Germany

[73] Assignee: Bayer Aktiengesellschaft, Leverkusen, Fed. Rep. of Germany

[21] Appl. No.: 32,255

[22] Filed: Apr. 23, 1979

Related U.S. Application Data

[63] Continuation of Ser. No. 894,556, Apr. 7, 1978, abandoned, which is a continuation of Ser. No. 419,665, Nov. 28, 1973, abandoned.

[30] Foreign Application Priority Data

Nov. 28, 1972 [DE] Fed. Rep. of Germany ....... 2258276

[51] Int. Cl.$^3$ .......................................... C07D 249/06
[52] U.S. Cl. .............................. 542/458; 252/301.22; 542/462
[58] Field of Search .............................. 542/458, 462; 252/301.22

[56] References Cited

U.S. PATENT DOCUMENTS

| | | | |
|---|---|---|---|
| 3,761,470 | 9/1973 | Strobel et al. | 542/462 |
| 3,816,413 | 6/1974 | Kirchmayr | 542/462 |
| 3,862,179 | 1/1975 | Kabas et al. | 252/301.22 |

*Primary Examiner*—Arthur P. Demers
*Attorney, Agent, or Firm*—Sprung, Felfe, Horn, Lynch & Kramer

[57] ABSTRACT

The subject matter are triazolyl-stilbenes of the formula

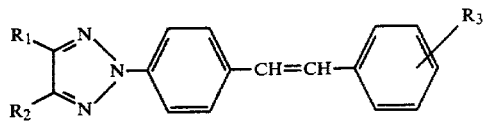

wherein $R_1$ represents an optionally substituted styryl, biphenylyl or naphthyl radical, $R_2$ represents hydrogen, halogen, or an alkyl or phenyl radical and $R_3$ represents nitrile, carboxyl or carboxylic acid ester, as well as their preparation and their use as optical brighteners.

12 Claims, No Drawings

TRIAZOLYL-STILBENES

This is a continuation, of Ser. No. 894,556 filed Apr. 7, 1978 now abandoned, which is a continuation of Ser. No. 419,665 filed Nov. 28, 1973, now abandoned.

The present invention relates to triazolyl-stilbenes of the formula

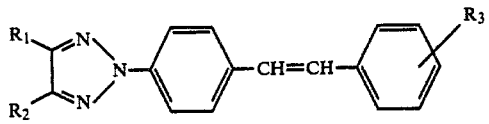

wherein
- $R_1$ denotes an optionally substituted styryl, biphenylyl or naphthyl radical,
- $R_2$ denotes hydrogen, halogen, an alkyl radical or a phenyl radical and
- $R_3$ denotes nitrile, carboxyl or carboxylic acid ester and their manufacture and use as brighteners.

Suitable substituents of the radicals $R_1$ are halogen, alkyl groups, especially those with 1–4 C atoms, nitrile, carboxyl or carboxylic acid ester groups. Preferred radicals $R_2$ are hydrogen, chlorine, bromine or alkyl with 1–4 C atoms.

Preferred compounds of the formula I are those of the formula

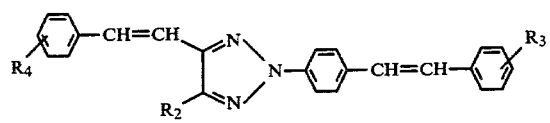

in which
- $R_4$ represents hydrogen, halogen, especially chlorine, an alkyl group with 1–4 C atoms, nitrile, the carboxyl group or a carboxylic acid alkyl ester group, whilst
- $R_2$ and $R_3$ have the abovementioned meaning.

Amongst the compounds of the formula II there should especially be singled out the compounds of the formula

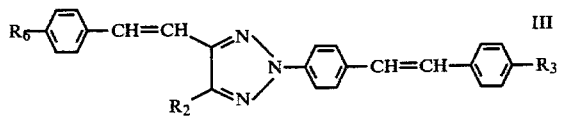

in which
- $R_6$ represents hydrogen, chlorine and preferably nitrile, the carboxyl group or a carboxylic acid alkyl ester group, whilst
- $R_3$ and $R_2$ have the abovementioned meaning.

The carboxylic acid ester groups mentioned are preferably alkyl esters of which the alkyl group contains 1–4 C atoms.

The new triazolyl-stilbenes I can be manufactured in various ways.

Those triazolyl-stilbenes I in which $R_2$ represents hydrogen or an alkyl radical can be obtained either by directly cyclising stilbene-hydrazonoximes of the formula

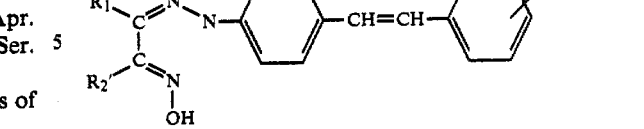

wherein
- $R'_2$ represents hydrogen or an alkyl radical and
- $R_1$ and $R_3$ have the indicated meaning by the action of suitable dehydrating agents, to give I, or by first converting the stilbene-hydrazonoximes with the aid of dehydrating agents into the triazolyl-stilbene-N-oxides of the formula

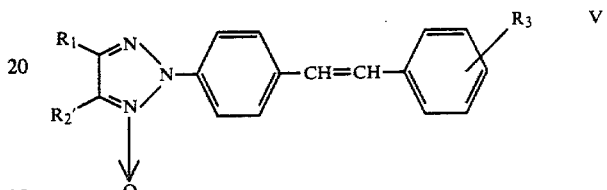

in which
- $R_1$, $R'_2$ and $R_3$ have the abovementioned meaning and subsequently converting these by reduction into the triazoles I.

The cyclodehydration of the oximinohydrazones IV to give the triazoles I can be carried out with the aid of processes which are in themselves known, for example by the action of acid chlorides or acid anhydrides, such as acetic anhydride, benzoyl chloride, cyanuric chloride or other cyclising agents, such as urea, without solvents or in solvents. Suitable solvents are, for example, excess acetic anhydride, acetic acid, dimethylformamide, dimethylsulphoxide, pyridine and technical pyridine bases, and glycol methyl ether acetate, individually or as mixtures with one another. In most cases it is necessary to add bases such as sodium acetate, potassium acetate, trimethylamine, triethylamine, benzyldimethylamine pyridine or higher pyridine homologues.

The cyclodehydrogenation of the oximinohydrazones IV to give the triazole-N-oxides V is appropriately carried out in solvents which are inert under the reaction conditions used and towards the oxidising agents chosen, for example pyridine, higher pyridine bases, dimethylformamide, dimethylsulphoxide, acetic acid and their mixtures with water.

Suitable dehydrogenating agents are, inter alia, copper-II salts such as copper acetate, copper formate and copper sulphate, complex copper-II compounds, lead dioxide, lead tetraacetate, sodium bichromate and potassium bichromate, potassium ferricyanide, hydrogen peroxide and potassium peroxydisulphate.

An industrially preferred embodiment consists of the dehydrogenation of IV, in pyridine or technical pyridine bases, with copper-II salts such as copper sulphate, copper chloride or copper acetate, and in these cases it can be desirable to blow in air in order to save copper salt.

The subsequent reduction of the triazole-N-oxides V can be carried out by means of zinc dust in acetic acid or mineral acid solution or suspension, or by tin granules or tin-II chloride in mineral acids.

The triazolyl-stilbenes corresponding to the formula I, in which $R_2$ represents halogen, are obtained from the triazole-N-oxides of the formula

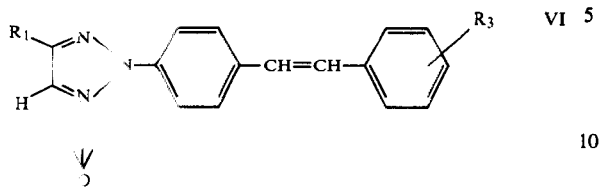

in which $R_1$ and $R_3$ have the abovementioned meaning by halogenation and deoxidation, preferably using halogenating agents which also act as dosoxidising agents in the same batch.

Possible halogenating agents of this nature are: phosphorus oxychloride and phosphorus trichloride by themselves or in the presence of bases such as trimethylamine, triethylamine, benzyldimethylamine, dimethylformamide or dimethylacetamide; phosphorus pentachloride and also mixtures of chlorine and phosphorus trichloride, phosphorus tribromide, thionyl chloride or sulphuryl chloride or mixtures of sulphur dioxide and chlorine, and also pyridine hydrochloride, pyridine hydrobromide and mixtures of hydrogen halide acids with ether bases.

The starting compounds IV required for the reactions mentioned can be obtained by condensing 4-hydrazinostilbenes of the formula

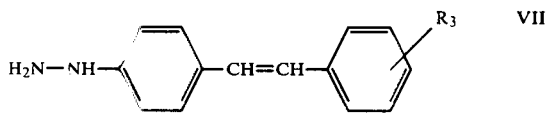

in which $R_3$ has the initially mentioned meaning, with α-oximinoketones of the formula

in which $R_1$ and $R'_2$ have the indicated meaning.

The reaction of VII with VIII is appropriately carried out in organic solvents, especially alcohols or aqueous alcohols, with acids (formic acid, acetic acid, phosphoric acid and others) as the catalyst, at between room temperature and about 80° C.

Examples of stilbene compounds VII are, inter alia, 4-hydrazino-4'-cyano-stilbene, 4-hydrazino-2'-cyanostilbene, 4-hydrazinostilbene-4'-carboxylic acid and its alkyl esters.

Examples of suitable oximinoketones VIII are: oximinobenzalacetone, p- and o-chloro-oximinobenzalacetone, p- and o-methyl-oximinobenzalacetone, 2,4-dichloro-oximinobenzalacetone, 2-oximino-5-phenyl-penten-(4)-one-(3), oximino-propiobiphenyl, 4'-chloro- and 4'-methyl oximinopropiobiphenyl, oximinoacetobiphenyl, oximino-α- and -β-propionaphthone and oximino-α- and -β-acetonaphthone.

Instead of carrying out the triazine cyclisation as the last step of the synthesis it is frequently desirable to synthesise this ring in an earlier stage. Thus, for example, it is advantageously possible to convert the hydrazones from 4-hydrazinobenzoic acid and the oximinoketones VIII, which correspond to the formula

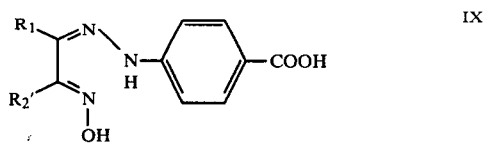

in which $R_1$ and $R'_2$ have the indicated meaning, analogously to the procedures already described, into the triazolyl-benzoic acids of the formula X, in which $R_1$ and $R_2$ have the initially indicated meaning

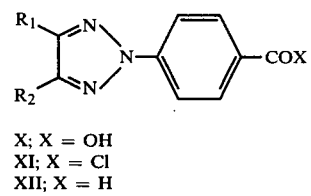

X; X = OH
XI; X = Cl
XII; X = H that is to say, it is possible to manufacture IX either directly by cyclodehydration by means of acylating agents or by cyclodehydrogenation to the particular N-oxido-triazolylbenzoic acid and its reduction or, in the case that $R_2$ denotes halogen, through treatment of these N-oxido-triazolylbenzoic acids with the halogenating agents mentioned.

The triazolylbenzoic acids X thus obtainable are easily converted into the triazolyl-benzaldehydes XII, which can be used for linking to an ethylene double bond, for example by first converting the acids X into the acid chlorides XI with the aid of thionyl chloride in solvents such as chlorobenzene, toluene or xylene, and then reducing the acid chlorides according to the Rosenmund process.

The triazolyl-stilbenes I according to the invention are obtained from the aldehydes of the formula XII by condensation with activated benzyl compounds of the formula

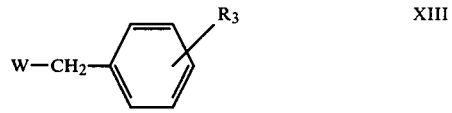

wherein

W represents nitrile, carboxyl, a carboxylic acid ester or the radical of a phosphonic acid diethyl ester and $R_3$ has the initially mentioned meaning, in the presence of basic agents.

Preferred benzyl compounds are the benzylphosphonic acid dialkyl esters, especially those whereof the alkyl radical contains 1–4 C atoms.

If the two phenyl radicals of the triazolyl-stilbene compounds of the formula II contain identical substituents in identical positions, for example o—CN, p—CN or p—COOCH$_3$, it is advisable to synthesise both ethylene groups together in the last step of the synthesis. This is done, advantageously, by condensation of the phenyl-triazole-dialdehydes of the formula

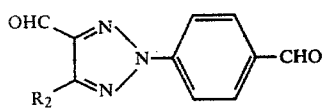   XIV in which
R$_2$ has the abovementioned meaning
with a two-fold molar amount of the benzylphosphonic acid dialkyl esters XIII in the presence of basic agents.

The dialdehydes XIV mentioned can (analogously to the reaction sequence X→XII) be obtained from the phenyltriazolyldicarboxylic acids XV.

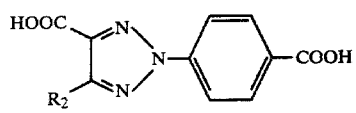   XV in which
R$_2$ has the abovementioned meaning.

The new triazolyl-stilbene compounds of the formula I are colourless to greenish-tinged white crystalline substances which possess good affinity to high molecular synthetic organic substances. They dissolve in most organic solvents to give a colourless solution having a strong blue to reddish-tinged blue fluorescence and are suitable for whitening fibres, filaments, woven fabrics, films and other structures of polyolefines, polyacrylonitrile, polyvinyl chloride, polyamides and especially polyesters, such as polyterephthalic acid glycol ester.

They can be used in the customary manner, for example in the form of aqueous solutions and dispersions or as solutions in organic solvents, such as glycol monomethyl ether, dimethylformamide or diglycol dimethyl ether.

They can further advantageously be incorporated into melt compositions and spinning compositions which are used for the manufacture of fibres, films or mouldings. The amounts to be used can easily be determined by preliminary experiments; they lie in the range of 0.001 to 0.5% relative to the weight of the material to be brightened.

EXAMPLE 1 a 55 g of 4-[4-styryl-v-triazolyl-(2)]-benzaldehyde and 53 g of 4-cyano-benzylphosphonic acid diethyl ester are dissolved in 450 ml of dimethylformamide. A solution of 12 g of sodium methylate in 30 ml of methanol is gradually added dropwise at 40° C., whilst stirring, and the mixture is kept at 50° C. for a further hour. Finally, 450 ml of water are added dropwise and the almost colourless crude product (60 g) which has separated out as crystals is filtered off, washed with methanol until free of alkali and purified by recrystallisation from 500 ml of chlorobenzene with addition of fuller's earth. 50 g of 4-[4-styryl-v-triazolyl-(2)]-4'-cyanostilbene are obtained in the form of greenish-tinged colourless crystals which dissolve in dimethylformamide to give a colourless solution with a strong reddish-tinged blue fluorescence.

Analogously, the triazolylbenzaldehyde derivatives XII on condensation with p- and o-cyano- or p-carbomethoxy- and p-carboethoxy-benzylphosphonic acid dialkyl esters yield the triazolyl-stilbene derivatives listed under 1 b–1 u in the table which follows.

| Example 1 | R$_1$ | R$_2$ | R$_3$ | Fluorescence colour in dimethylformamide |
|---|---|---|---|---|
| a | ⌬—CH=CH | H | p-CN | reddish-tinged blue |
| b | " | " | o-CN | strongly reddish-tinged blue |
| c | " | " | p-COOCH$_3$ | reddish-tinged blue |
| d | Cl—⌬—CH=CH— | " | p-CN | reddish-tinged blue |
| e | " | " | o-CN | strongly reddish-tinged blue |
| f | " | " | p-COOCH$_3$ | reddish-tinged blue |
| g | H$_3$C—⌬—CH=CH— | " | p-CN | blue |
| h | ⌬(Cl)—CH=CH— | " | p-CN | reddish-tinged-blue |
| i | " | " | p-COOCH$_3$ | reddish-tinged blue |
| k | ⌬—⌬— | CH$_3$ | p-CN | slightly reddish-tinged blue |
| l | " | " | o-CN | reddish-tinged blue |
| m | " | " | p-COOCH$_3$ | reddish-tinged blue |
| n | naphthyl— | CH$_3$ | p-CN | reddish-tinged blue |
| o | " | " | p-COOCH$_3$ | reddish-tinged blue |
| p | " | " | p-COOC$_2$H$_5$ | reddish-tinged blue |
| q | naphthyl— | " | p-CN | blue |
| r | " | " | p-COOCH$_3$ | blue |
| s | ⌬—CH=CH | Cl | p-CN | slightly reddish-tinged blue |
| t | " | " | o-CN | reddish-tinged blue |
| u | " | " | p-COOCH$_3$ | reddish-tinged blue |

4-[4-Styryl-v-triazolyl-(2)]-benzaldehyde was manufactured as follows:

A suspension of 285 g of 4-hydrazino-benzoic acid hydrochloride in 1.5 l of 50% strength aqueous ethanol is treated with 250 g of sodium acetate at room temperature, whilst stirring. Thereafter, 500 ml of 50% strength acetic acid are run in, followed by a solution of 290 g of oximinobenzalacetone in 800 ml of ethanol. The reaction mixture is stirred for 2 hours at 30°–35° C. and for a further 6 hours at room temperature. The orange-coloured oximinohydrazone which has separated out is filtered off and rinsed with 50% strength ethanol. After drying (in vacuo) 440 g of oximinohydrazone of melting point 215°–218° C. are obtained.

440 g of the oximinohydrazone thus produced are stirred with 350 g of anhydrous sodium acetate in 4 l of dimethylformamide. The dropwise addition of 600 g of acetic anhydride is started at room temperature, and in the course thereof the temperature rinses to approx. 45° C. Thereafter the mixture is stirred for a further hour at this temperature and for a further 4 hours at 85°–95° C. The cyclisation is then complete and the viscous orange-yellow reaction mixture is introduced into 15 l of water at approx. 60°–70° C. The resulting crystal suspension is rendered acid to Congo Red by means of concentrated hydrochloric acid (consumption approx. 700 ml) and the crude triazolylbenzoic acid is filtered off. It is purified by redissolving in 50% strength methanol using active charcoal, and adding the amount of sodium hydroxide solution necessary to form the sodium salt. The solution is filtered and acidified with hydrochloric acid, and sodium chloride is added. After cooling, the 4-[4-styryl-v-triazolyl-(2)]-benzoic acid which has separated out as crystals is filtered off, washed with cold water and dried.

318 g of colourless crystals of melting point 252°–254° C. are obtained.

318 g of 4-[4-styryl-v-triazolyl-(2)]-benzoic acid in 1 l of chlorobenzene are stirred with 200 ml of freshly distilled thionyl chloride at 60°–70° C. for 2 hours and the resulting solution is clarified with dry fuller's earth and then concentrated under reduced pressure to about half the initial volume. It is cooled to 0° C. and left to stand for 2 hours, and the 4-[4-styryl-v-triazolyl-(2)]-benzoyl chloride which has crystallised out in the form of colourless crystals is filtered off and dried at room temperature. The yield is 277 g. Melting point 146°–147° C.

2.7 l of xylene are mixed with a catalyst consisting of 50 g of barium sulphate coated with 5% of palladium and 6 ml of a solution of 0.08 g of sulphur and 0.48 g of quinoline in xylene. The mixture is dried by distilling off about 150–200 ml of xylene under normal pressure whilst passing a slight stream of hydrogen through it. 277 g of 4-[4-styryl-v-triazolyl-(2)]-benzoyl chloride are rapidly introduced into the hot solution and a vigorous stream of hydrogen is passed through the reaction mixture at 118°–120° C. After 1½ to 2 hours the evolution of hydrogen chloride has largely ceased; the dissolved hydrogen chloride is removed by passing in nitrogen, the catalyst is removed from the hot solution by filtration and the hot filtrate is concentrated in a rotary evaporator. 239 g of colourless, crystalline residue containing 92% of 4-[4-styryl-v-triazolyl-(2)]-benzaldehyde are obtained and can be used, without further purification, for condensation reactions with benzylphosphonic acid ester.

The crude aldehyde can be purified easily via its bisulphite adduct and then melts at 140°–142° C.

If instead of oximino-benzalacetone equimolar amounts of p-chloro-, p-methyl- and o-chloro-oximinobenzalacetone or oximinopropiobiphenyl or oximino-propio-β-naphthyl are used, the triazolyl-benzoic acids, triazolyl-benzoyl chlorides and triazolyl-benzaldehydes listed in the table which follows are obtained analogously and in similar yields.

| $R_1$ | $R_2$ | Z = COOH | Z = COCl | Z = CHO |
|---|---|---|---|---|
| C₆H₅—CH=CH— | H | 260°–261° C. | 147° C. | 140°–142° C. |
| Cl—C₆H₄—CH=CH— | H | 272°–274° C. | 182°–184° C. | 157°–159° C. |
| CH₃—C₆H₄—CH=CH— | H | 270°–272° C. | 161°–164° C. | 154°–156° C. |
| (o-Cl)C₆H₄—CH=CH— | H | 257°–259° C. | 155°–157° C. | 151°–153° C. |
| biphenyl— | CH₃ | 292°–294° C. | 208°–209° C. | 149°–150° C. |

-continued

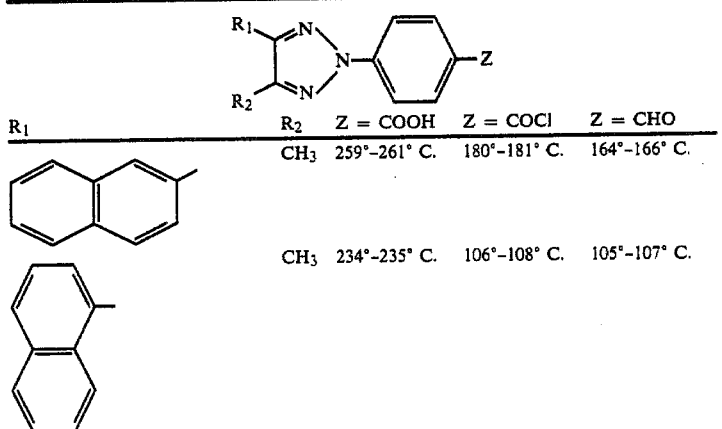

| R₁ | R₂ | Z = COOH | Z = COCl | Z = CHO |
|---|---|---|---|---|
| 2-naphthyl | CH₃ | 259°–261° C. | 180°–181° C. | 164°–166° C. |
| 1-naphthyl | CH₃ | 234°–235° C. | 106°–108° C. | 105°–107° C. |

The 4-[4-styryl]5-chloro-v-triazolyl-(2)]-benzaldehyde used to manufacture the triazolyl-stilbene compounds 1s–u was prepared as follows:

155 g of oximinobenzalacetone-p-carboxyphenylhydrazone are introduced into a solution of 250 g of crystalline copper sulphate in 375 ml of water and 750 ml of pyridine at 60° C., whilst stirring. The mixture is then stirred for a further 2 hours at 90°–95° C., the bulk of the pyridine is distilled off and dilute hydrochoric acid is added to the light brown suspension obtained until it gives a distinctly acid reaction to Congo Red.

After cooling, the product which has precipitated is filtered off, and washed with dilute hydrochloric acid and subsequently with water. After drying, 124 g of 4-[4-styryl-1-oxido-v-triazolyl-(2)]-benzoic acid, which can be purified by recrystallisation from aqueous glycol monomethyl ether, are obtained. Melting point 233°–234° C.

124 g of 4-[4-styryl-1-oxido-v-triazolyl-(2)]-benzoic acid are introduced into 300 ml of thionyl chloride. The mixture is stirred for 2 hours at 60° C., during which the starting substance dissolves, and is heated for ½ hour under reflux. The thionyl chloride is distilled off under reduced pressure and the residue is purified by recrystallisation from 100 ml of chlorobenzene with the addition of a little dry fuller's earth. 78 g of 4-[4-styryl-5-chloro-v-triazolyl-(2)]-benzoyl chloride of melting point 155°–156° C. are obtained.

78 g of 4-[4-styryl-5-chloro-v-triazolyl-(2)]-benzoyl chloride in 850 ml of xylene are reduced with hydrogen analogously to the procedure described above. In order to avoid losses in yield, the hydrogenation is stopped immediately the evolution of hydrogen chloride begins to subside. After filtering off the catalyst, the xylene solution is concentrated under reduced pressure and 57 g of 4-[4-styryl-5-chloro-v-triazolyl-(2)]-benzaldehyde, which can be employed without further purification for the further reaction, are obtained. It can be obtained pure, in the form of colourless crystals of melting point 130°–132° C., by recrystallisation from butanol.

EXAMPLE 2a 20.1 g of 4-[4-formyl-v-triazolyl-(2)]-benzaldehyde and 60 g of 4-methoxycarbonyl-benzylphosphonic acid diethyl ester are dissolved in 300 ml of dimethylformamide at 50° C. 12 g of sodium methylate are introduced whilst stirring, and the mixture is stirred for a further hour at 60° C. and diluted with 600 ml of 50% strength aqueous methanol. The crystals which have precipitated are filtered off, washed with methanol and recrystallized from hot o-dichlorobenzene, using fuller's earth. 28 g of 4-[4'-p-methoxycarbonyl-styryl-v-triazolyl(2)]-4'-methoxycarbonyl-stilbene are obtained in the form of greenish-tinged white crystals.

If instead of methoxycarbonyl-benzylphosphonic acid diethyl ester an equimolar amount of p-ethoxycarbonyl- or p-cyano-benzylphosphonic acid diethyl ester is used, the compounds listed under b and c in the table which follows are obtained. The saponification of the carboxylic acid esters 2a or b with 78% strength sulphuric acid yields the free dicarboxylic acid 2d. If 4-[4-formyl-5-methyl- or -5-chloro-v-triazolyl-(2)]-benzaldehyde is condensed analogously with p-methoxycarbonyl- or p-cyano-benzylphosphonic acid diethyl ester or dimethyl ester in the manner described, the styrytriazolyl-stilbene compounds 2e–h are obtained.

| Example 2 | R₂ | Y | Fluorescence colour in dimethylformamide |
|---|---|---|---|
| a | H | COOCH₃ | slightly reddish-tinged blue |
| b | H | COOC₂H₅ | slightly reddish-tinged blue |
| c | H | CN | blue |
| d | H | COOH | blue |
| e | CH₃ | COOCH₃ | blue |
| f | CH₃ | CN | blue |
| g | Cl | COOCH₃ | slightly reddish-tinged blue |
| h | Cl | CN | blue |
| i | C₆H₅ | COOCH₃ | reddish-tinged blue |
| k | C₆H₅ | CN | reddish-tinged blue |

4-[4-Formyl-v-triazolyl-(2)]-benzaldehyde is manufactured as follows:

380 g of 4-hydrazinobenzoic acid hydrochloride are suspended in 1.5 l of 50% strength aqueous methanol at room temperature. 220 g of sodium acetate, 100 ml of 50% strength acetic acid and 185 g of oximinoacetone are added to the suspension. The mixture is stirred for a further 4 hours at room temperature and the yellow precipitate is filtered off and dried in air. The yield of oximinoacetone(p-carboxyphenyl)-hydrazone (melting point 214°–216° C., decomposition) is 450 g.

The hydrazone obtained is introduced into a solution of 1 kg of crystalline copper sulphate in 1.6 l of water and 2.6 l of pyridine at 60° C., whilst stirring. The mixture is stirred for a further 2 hours at 90°–95° C., the bulk of the pyridine is then distilled off, 1.2 l of water are added to the residual suspension and the mixture is acidified by adding hydrochloric acid until it reacts acid to Congo Red. The resulting 4-[4-methyl-1-oxido-v-triazolyl-(2)]-benzoic acid is filtered off and thoroughly washed with dilute hydrochloric acid and water. After drying, 440 g of yellowish-tinged grey powder of melting point 223°–224° C. are obtained.

The resulting 4-[4-methyl-1-oxido-v-triazolyl-(2)]-benzoic acid (440 g) is dissolved in a mixture of 2 l of glacial acetic acid and 100 ml of water. 140 g of zinc dust are introduced over the course of 2 hours at 100°–105° C., whilst stirring well, and the batch is additionally boiled for 2 hours under reflux. Thereafter, 150 ml of concentrated hydrochloric acid are added followed, after half an hour, by 1 l of water. After cooling to room temperature, the 4-[4-methyl-v-triazolyl-(2)]-benzoic acid which has precipitated is filtered off and purified by reprecipitation from dilute sodium hydroxide solution. The yield is 320 g of melting point 244°–246° C.

320 g of 4-[4-methyl-v-triazolyl-(2)]-benzoic acid are dissolved in 7 l of hot 1 N hydroxide solution. 640 g of potassium permanganate are introduced in portions over the course of 5 to 6 hours at 95° C., whilst stirring; a slight excess of permanganate is reduced by adding a little ethanol. The hot solution is clarified by removing the magnanese dioxide formed and the filtrate is acidified with hydrochloric acid. After cooling, the 4-[4-carboxy-v-triazolyl-(2)]-benzoic acid which has precipitated as colourless crystals is filtered off, rinsed with a little cold water and dried.

280 g of melting point 314°–315° C. are obtained.

280 g of 4-[4-carboxy-v-triazolyl-(2)]-benzoic acid are introduced into 1 l of thionyl chloride at 60°–70° C. The mixture is kept at this temperature until the material has completely dissolved; thereafter, the unconsumed thionyl chloride is distilled off under reduced pressure. The residue is recrystallised from ligroin-benzene (2:1). 254 g of 4-[4-chlorocarbonyl-v-triazolyl-(2)]-benzoyl chloride are thus obtained in the form of colourless crystals of melting point 65°–66° C.

1.5 l of xylene are mixed with 50 g of the hydrogenation catalyst described in Example 1. The mixture is dried by distilling off approx. 150 ml of xylene, whilst passing a slight stream of hydrogen through it. 254 g of 4-[4-chlorocarbonyl-v-triazolyl-(2)]-benzoyl chloride are now introduced into the hot mixture and hydrogen is vigorously passed through the reaction mixture at 118°–120° C. After 3 to 4 hours the evolution of hydrogen chloride ceases; dissolved hydrogen chloride is expelled by passing in nitrogen. The reaction mixture is heated to the boil and the catalyst is filtered off. A large part of the product crystallises out of the filtrate after it has cooled; it is filtered off and the mother liquors are evaporated to dryness. The colourless crystalline residue is stirred with a little petroleum ether and filtered off. A total of 180 g of 4-[4-formyl-v-triazolyl-(2)]-benzaldehyde is thus obtained in the form of colourless crystals of melting point 181°–182° C.

Analogously, 4-[4-carboxy-5-methyl-v-triazolyl-(2)]-benzoic acid yields 4-[4-formyl-5-methyl-v-triazolyl-(2)]-benzaldehyde by Rosenmund reduction of the dicarboxylic acid chloride, 4-[4-carboxy-5-phenyl-v-triazolyl-(2)]-benzoic acid yields 4-[4-formyl-5-phenyl-v-triazolyl(2)]-benzaldehyde and 4-[4-carboxy-5-chloro-v-triazolyl-(2)]-benzoic acid yields 4-[4-formyl-5-chloro-v-triazolyl-(2)]-benzaldehyde.

These dialdehydes or their precursors are colourless crystals, of which the melting points are listed in the table which follows:

|  | Z = COOH | Z = COCl | Z = CHO |
|---|---|---|---|
| $R_2 = CH_3$ | 331° C. (dec.) | 101° C. | 148°–149° C. |
| $R_2 = C_6H_5$ | 278°–280° C. | 141° C. | 147°–149° C. |
| $R_2 = Cl$ | 340° C. (dec.) | 98°–100° C. | 143°–145° C. |

EXAMPLE 3

(a) 20.1 g of 4-[4-formyl-v-triazolyl-(2)]-benzaldehyde, 30 g of 4-methoxycarbonyl-benzylphosphonic acid diethyl ester and 27.5 g of 4-cyano-benzylphosphonic acid diethyl ester are dissolved in 300 ml of dimethylformamide at 50° C. Thereafter, 12 g of sodium methoxylate are stirred in; the reaction mixture is additionally kept at 60° C. for 1 hour and is then diluted with 600 ml of 50% strength aqueous methanol. The crystalline precipitate which has separated out is filtered off, washed with methanol and recrystallised from o-dichlorobenzene with addition of fuller's earth. 26 g of a mixture which consists of the triazolyl-stilbene compounds 2a and 2c and the compounds of the formulae

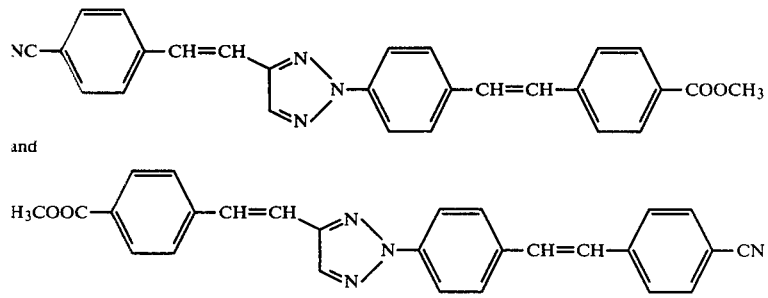

and which dissolves in dimethylformamide, to give a colourless solution with a strong blue fluorescence, are obtained.

(b) If 4-[4-formyl-v-triazolyl-(2)]-benzaldehyde is reacted with a two-fold molar amount of 2-cyanobenzylphosphonic acid diethyl ester, the triazolyl-stilbene compound of the formula

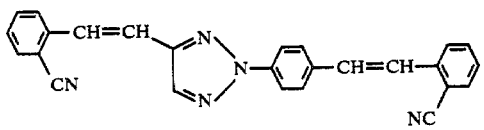

is obtained in the form of greenish-tinged white crystals which give a strong blue fluorescence in dimethylformamide.

EXAMPLE 4

A fabric of polyester fibres is padded with an aqueous liquor which contains, per liter, 1 g of a commercially available dispersing agent based on fatty alcohol polyglycol ethers, 1 g of a commercially available wetting agent based on alkylnaphthalenesulphonic acids, 4 g of alginate thickener and a dispersion of 1 g of one of the triazolyl-stilbene compounds listed in Examples 1, 2 and 3 in 25 ml of triethanolamine. The fabric is squeezed out to a weight increase of 100% and heated to 190° C. for ½ minute. After washing and drying, the polyester fabric shows a strong, clear brightening of very good fastness to light, washing and chlorite.

EXAMPLE 5

Using a liquor ratio of 1:40, polyester yarn is introduced into a bath which contains, per liter, 1.5 g of sodium oleylsulphonate, 0.75 g of formic acid and 0.1 g of one of the triazolyl-stilbene compounds described in Example 1. The bath is brought to 125° C. over the course of 30 minutes with the vessel closed and is agitated for 45 minutes at this temperature. Finally, the yarn is rinsed and dried. It shows a strong, clear brightening of very good fastness to light, washing and chlorite.

EXAMPLE 6

Polyamide 6 fabric is agitated for 30 minutes, using a liquor ratio of 1:40, in an aqueous bath at 85°–90° C. which contains, per liter, 0.1 g of the brightener 1c, 1 f, 1 i or 1 u. After rinsing and drying, the fabric shows a strong, clear brightening of good fastness properties.

EXAMPLE 7

6 kg of terephthalic acid dimethyl ester and 5 l of ethylene glycol are mixed with 0.05% of zinc acetate and 0.03% (relative to terephthalic acid dimethyl ester) of one of the triazolyl-stilbene compounds listed in Examples 2 and 3, in a stirred autoclave. The autoclave is heated to 180° C. whilst stirring and the methanol split off is distilled off. After 1 hour the temperature is raised to 200° C. and after a further 45 minutes to 220° C. After a total of 2¾ hours the trans-esterification is complete and the product thus obtained is passed under nitrogen into an autoclave heated to 275° C. for pre-condensation. Excess glycol is distilled off through a condenser. After 45 minutes a slight vacuum is first applied and this is improved to (less than) 1 mm Hg over the course of a further 45 minutes. After 2½ hours, the polycondensation is complete. The resulting product is subsequently spun into filaments in a known manner. The filaments thus produced show a strong, clear brightening of very good fastness to light and wet processing.

EXAMPLE 8

100 g of polyvinyl chloride suspension polymer of K-value 75–78, 2 g of barium-cadmium stearate, 0.5 g of a stabiliser based on dibutyl-tin dilaurate and 1 g of titanium dioxide (rutile) are homogenised on a hot mill at about 165°–170° C. and the resulting hide is subsequently pressed at 150°–170° C. under a pressure of 40–50 kg/cm² to give a sheet. The sheet thus produced has a slightly yellowish-white shade.

If, before milling on the hot mill, 0.08 g of the triazolyl-stilbene compound described in Example 1h or 1i is added to the mixture and the procedure indicated above is followed, a substantially lighter, very clear white shade is obtained, which shows no tendency to yellow.

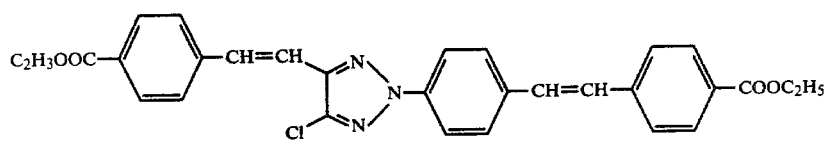

We claim:

1. A triazolyl-stilbene of the formula

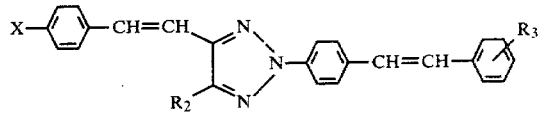

wherein
$R_2$ is H or Cl,
$R_3$ is p—CN, o—CN, p—COOCH$_3$ or p—COOC$_2$H$_5$, and
X is H, Cl, COOCH$_3$ or COOC$_2$H$_5$.

2. A triazolyl stilbene according to claim 1 of the formula

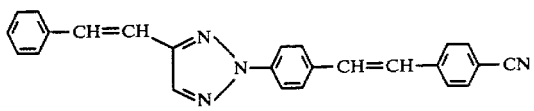

3. A triazolyl stilbene according to claim 1 of the formula

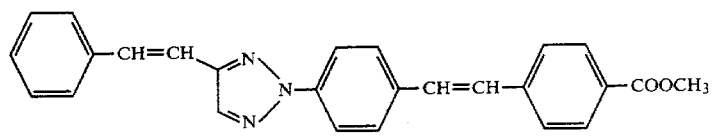

4. A triazolyl stilbene according to claim 1 of the formula

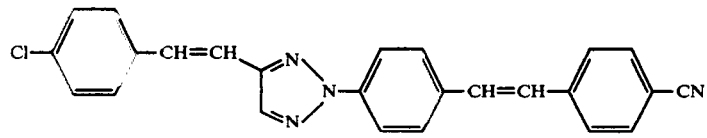

5. A triazolyl stilbene according to claim 1 of the formula

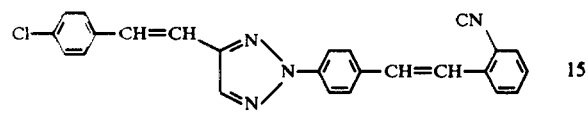

6. A triazolyl stilbene according to claim 1 of the formula

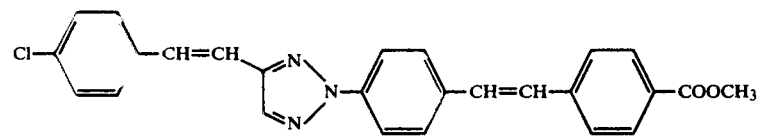

7. A triazolyl-stilbene according to claim 1 of the formula

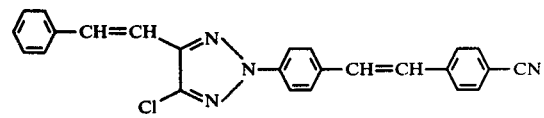

8. A triazolyl-stilbene according to claim 1 of the formula

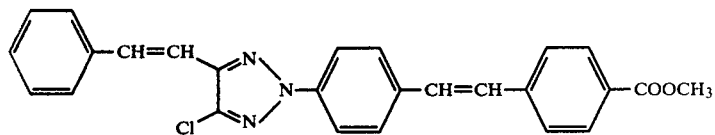

9. A triazolyl-stilbene according to claim 1 of the formula

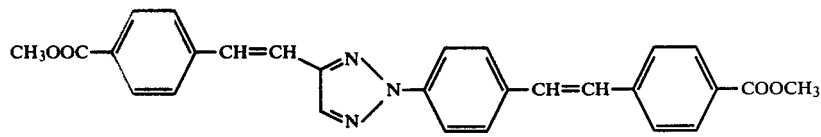

10. A triazolyl-stilbene according to claim 1 of the formula

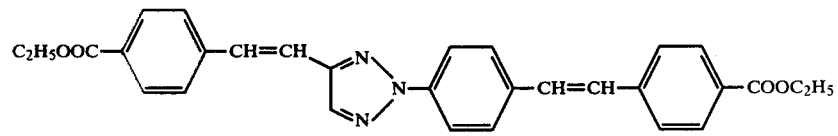

11. A triazolyl-stilbene according to claim 1 of the formula

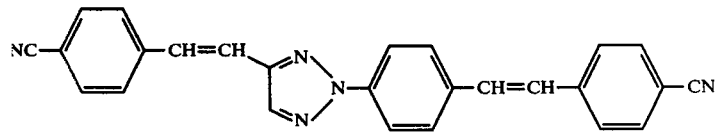

12. A triazolyl-stilbene according to claim 1 of the formula